(12) United States Patent
Tang (10) Patent No.: US 7,759,087 B1
(45) Date of Patent: Jul. 20, 2010

(54) METHOD OF INDEFINITE CULTURE OF HEPATITIS C VIRUS

(75) Inventor: Hengli Tang, Tallahassee, FL (US)

(73) Assignee: The Florida State University Research Foundation, Inc., Tallahassee, FL (US)

( * ) Notice: Subject to any disclaimer, the term of this patent is extended or adjusted under 35 U.S.C. 154(b) by 600 days.

(21) Appl. No.: 11/536,324

(22) Filed: Sep. 28, 2006

Related U.S. Application Data (60) Provisional application No. 60/721,211, filed on Sep. 28, 2005.

(51) Int. Cl.
*A01N 1/02* (2006.01)
*C12P 21/00* (2006.01)

(52) U.S. Cl. .................. 435/41; 435/40.51; 435/42; 435/325; 435/2

(58) Field of Classification Search .................. None
See application file for complete search history.

(56) References Cited

OTHER PUBLICATIONS

Alan Cann at the website http://www.microbiologybytes.com/LabWork/grow/grow1.htm, 2007, p. 1.*
Clark et al. J. Med. Chem. 2005, vol. 48, pp. 5504-5508.*
Stuyver et al. J. Virol. 2003, vol. 77, No. 19, pp. 10689-10694.*
Ma et al. The Journal of biological Chemistry, 2007, vol. 282, No. 41, pp. 29813-29820.*

\* cited by examiner

*Primary Examiner*—Zachariah Lucas
*Assistant Examiner*—Bao Qun Li
(74) *Attorney, Agent, or Firm*—Allen, Dyer, Doppelt, Milbrath & Gilchrist, P.A.

(57) ABSTRACT

The invention discloses a method of maintaining hepatitis C virus (HCV) growing indefinitely in cell culture. The method includes providing a culture of cells susceptible to infection by HCV; introducing to the cell culture an inoculum containing an infective dose of HCV; contacting the inoculated cell culture with a growth medium containing an excess of uridine and cytidine; and changing spent growth medium with fresh growth medium containing the excess of uridine and cytidine on a predetermined schedule.

4 Claims, 11 Drawing Sheets

METHOD OF INDEFINITE CULTURE OF HEPATITIS C VIRUS

FIELD OF THE INVENTION

The present invention relates to the field of infectious diseases and, more particularly, to a method of culturing hepatitis C virus (HCV).

BACKGROUND OF THE INVENTION

Hepatitis C virus (HCV) is a positive-strand RNA virus that infects more than 170 million people worldwide. The infection mainly affects the liver and leads to both acute and chronic liver diseases including cirrhosis and hepatocellular carcinoma (HCC). HCV replication has proved to be a good model system for studies of virus-host cell interactions, as the virus often establishes a chronic infection that typifies the intricate relationship between a pathogen and its host.

Research on HCV infection in vitro has been hampered by lack of an efficient cell culture-based production and infection system. The very recent reports of production of infectious HCV particles in tissue culture will hopefully break through this barrier and usher in a new era of HCV research (13, 24, 30). Studies of HCV RNA replication, however, received a great boost with the development of the HCV subgenomic replicon system a number of years ago (1, 14). Many important questions about the RNA replication of the virus were answered through use of the replicon cells. Adaptive mutations that permit efficient RNA replication in cultured hepatoma cells as well as nonhepatic cell lines have been defined (1, 11, 31); critical components of replication have been mapped, and the data greatly complemented the limited in vivo data available previously (4, 10, 29). A novel mechanism by which HCV suppresses the innate antiviral responses to establish persistent replication has been uncovered (3). The replicon system is also being used extensively to evaluate antiviral agents such as small-molecular drugs (8) as well as small interfering RNAs (21). The validity of the replicon system for this purpose has been highlighted by the in vivo efficacy in humans of a small-molecule compound that was tested solely in the replicon without any animal efficacy study (12). Even though the future of the compound is uncertain because of in vivo toxicity issues, the excellent correlation between the replicon inhibition in vitro and the in vivo antiviral effect provided good proof of principle for both the class of the drug and the screening assay.

Various derivatives of the HCV replicon that harbor different reporter genes have been constructed to facilitate the measurement of replication by means of surrogate markers (11, 18, 28). Recently, a replicon cell line has been developed in which the green fluorescent protein (GFP) gene is inserted into the coding region of the NS5A gene without abolishing the ability of the RNA to replicate in Huh-7 cells (16). This line allowed direct visualization of fusion protein, NS5A-GFP, with fluorescence microscopy for study of the dynamics of the HCV replication complex in living cells, as NS5A is one of the nonstructural proteins believed to be in the replication complex. Co-localization of NS5A and newly synthesized viral RNA was observed.

A tight coupling between HCV replication and the physiological state of the host liver cells has been observed. In particular, a highly reproducible and reversible inhibitory effect of cell confluency on HCV replication was reported: high levels of HCV RNA and protein that can be detected in actively growing cells decrease dramatically when the replicon cells reach confluency. When the confluent cells are split into lower density, replication resumes, and HCV expression recovers (20, 22).

SUMMARY OF THE INVENTION

With the foregoing in mind, the present invention advantageously provides a method of maintaining a culture of HCV growing indefinitely.

Here we also report the development and validation of a new replicon assay that allows flow cytometry-based measurement of HCV expression. This assay measures NS5A-GFP expression in individual cells and is therefore not biased against reduced cell number in samples with cytostasis. Using this assay, combined with traditional viral RNA and protein analysis, we found that cell growth arrest is not the mechanism for cell confluency-based replicon inhibition. Instead, reduced nucleoside level in confluent cells can partly account for the inhibition.

An intimate relationship between hepatitis C virus (HCV) replication and the physiological state of the host liver cells has been reported. In particular, a highly reproducible and reversible inhibitory effect of high cell density on HCV replication was observed: high levels of HCV RNA and protein can be detected in actively growing cells but dec

FIG. 18 shows that RNA analysis confirms the results obtained with NS5A-GFP expression; GS4 cells were cultured under various conditions for 3 days before the total RNAs were extracted and subjected to northern analysis with a radioactively labeled DNA probe that is complementary to the 3' end of the NS5B and the 3' untranslated region of HCV 1 b; a single band of 9.6 Kb representing the viral genome was detected; a photograph of the RNA electrophoresis gel before northern transfer shows that equivalent amounts of RNA were loaded for each sample; lane 1: GS4 untreated, nonconfluent cells cultured in 10% serum; lane 2: 1 µM 2CMA; lane 3: 10 µg/ml aphidicolin; lane 4: 0% serum; lane 5: same as lane 1; lane 6: GS4 cells cultured under confluency; lane 7: GS4 cells cultured under confluency but with uridine and cytidine (200 µM each) added to the culture medium.

DETAILED DESCRIPTION OF THE PREFERRED EMBODIMENT

Materials and Methods

Compounds. Interferon-a (IFN-α), aphidicolin, uridine, and cytidine were purchased from Sigma. Cyclosporin A (Cs A) was purchased from Alexis Corporation (San Diego, Calif.). 2'-C-methyl-adenosine (2CMA) was a gift from Dr. Steve Carroll (Merck Inc.).

SiRNA. Hairpin siRNAs directed against the NS5B sequence of HCV 1b and the firefly luciferase gene were expressed in the hairpin format from a lentiviral vector as previously described (25). Viral vectors were produced in 293-T cells and viral transductions were done according to standard procedures.

Cell lines. Clone B and Huh.8 cells were obtained from Apath LLC through the NIH AIDS reagents program. The I/5A-GFP cell line was provided by Dr. Charles Rice. Replicon cells were routinely maintained in Dulbecco modified medium supplemented with antibiotics, 10% fetal bovine serum, and 500 µg/ml G418. Huh-7 cells were maintained in a similar medium but without the G418. When replicon cells were treated with various HCV inhibitors, the G418 was also omitted from the medium.

Flow cytometry and cell cycle analysis. Cells were routinely fixed in 2% paraformaldehyde before flow cytometry analysis, which was performed with a FACSCanto flow cytometer (BD Biosciences). Live cell sorting was performed under sterile conditions with a FACSAria flow cytometer (BD Biosciences). The approximately 5% of cells ($2\times10^7$ cells total) with the strongest GFP signal were sorted back for expansion at each round of live-cell sorting. For cell-cycle analysis, $1\times10^6$ cells were stained with 50 μg/ml propidium iodide in the presence of 200 μg/ml RNase A and 0.1% Triton X-100 for 30 minutes before being subjected to FACS analysis.

Microscopy. For confocal microscopy, the cells were seeded onto glass coverslips deposited in six-well plates. After treatment, cells were fixed in 4% paraformaldehyde on the coverslip, which was then mounted on a glass slide for microscopic observations. Fluorescence and DIC images of the cells were examined with a Zeiss LSM 510 Laser Scanning Confocal Microscope equipped with multi-photon laser and recorded with the accompanying LSMIB-3.2 software.

Antibodies and western blots. An anti-NS5A monoclonal antibody was purchased from Virogen (Boston, Mass.) and an anti-Ku86 monoclonal antibody from Sigma. A monoclonal antibody against GFP was obtained from Clontech/BD Biosciences. To detect membrane-associated HCV proteins, we directly lysed the replicon cells in SDS PAGE sample buffer. We used $2\times10^5$ cells per 160 μl of SDS PAGE sample buffer for all our western blotting experiments. Blotting and detection were all performed according to standard procedures. For detection of Ku86 signal, the membrane was first stripped of the NS5A signal by incubation in stripping buffer (100 mM 2mercaptoethanol, 2% SDS, 62.5 mM Tris-HCl, pH 6.7) for 30 minutes at 50° C.

RNA extraction and northern blots. Total RNA was extracted with TRIzol reagent (Invitrogen, San Diego, Calif.). Equal amounts of RNA (10 μg per sample) were loaded onto formaldehyde-containing agarose gels for electrophoresis. The transfer of RNA onto a nitrocellulose membrane, random labeling of a radioactive probe, and hybridization were all performed according to standard molecular-biology protocols. The probe for detecting HCV RNA is a cDNA fragment that corresponds to nucleotides 8024 to 9563 of HCV 1 b. The exposure and detection of the radioactive signal was done with a Storm 860 phosphor-imaging system (Amersham/GE Healthcare).

Results

Figure 1:
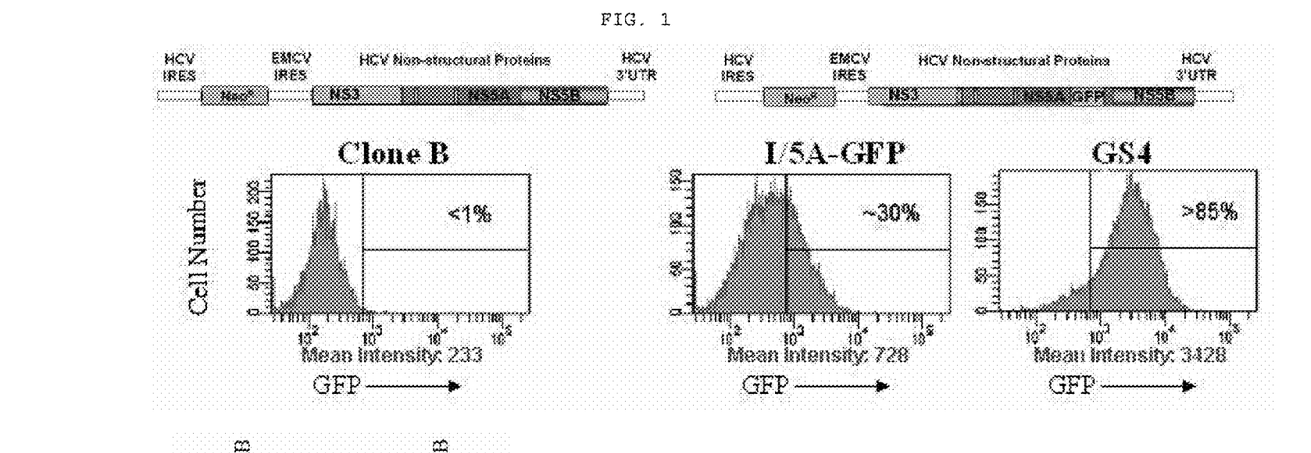
Figure 2:
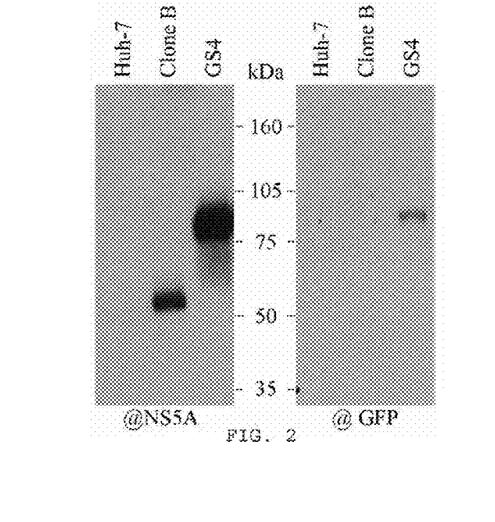
Figure 3:
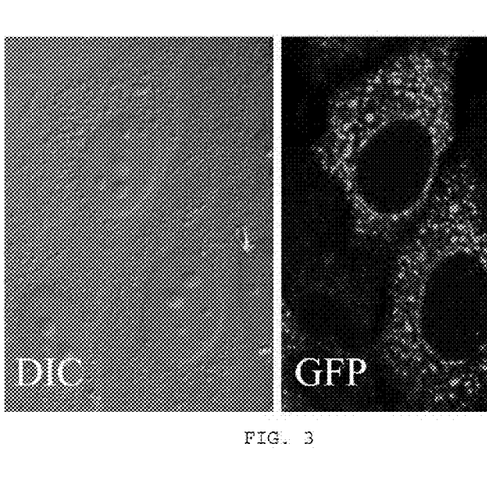

A novel GFP-based flow cytometry assay for HCV replication. Recently, a modified HCV replicon with the eGFP gene inserted into the coding region of NS5A has been generated for study of the subcellular localization of the HCV replication complex (16). In this replicon cell line (I/5A-GFP), the NS5A-GFP fusion protein exhibits properties of both the fluorescent protein and the HCV NS5A as it supports HCV replication and renders the cells harboring the hybrid replicon fluorescent under a fluorescence microscope. When we subjected I/5A-GFP cells to flow-cytometry analysis, we found the GFP signal of the majority (~70%) of the cells to be indistinguishable from that of Clone B, a replicon cell line without GFP but containing the same S2204I mutation in the NS5A gene (1) (FIG. 1). To obtain a cell line with minimal FACS-profile overlap with the GFP-negative replicon cells, we then performed consecutive rounds of cell sorting on I/5A-GFP-6 cells in which the cells with the strongest GFP were recovered. A population with no greater than 15% GFP-negative cells was obtained after four rounds of sorting and was used for the present study. We designated these cells GS4 (FIG. 1). Immunoblotting analysis using both anti-NS5A and anti-GFP antibodies revealed only one species of NS5A-GFP hybrid protein in these cells, indicating that no green fluorescence was contributed by unfused or truncated GFP proteins (FIG. 2). When examined under a fluorescence microscope, the green fluorescence of the GS4 cells exhibited the characteristic punctuate subcellular localization of HCV nonstructural proteins (FIG. 3).

Figure 4:
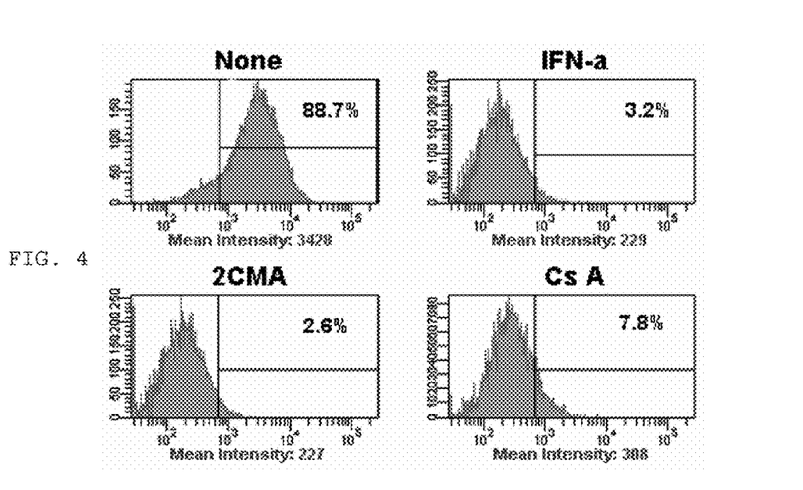
FIG. 4 shows that known HCV inhibitors inhibit NS5A-GFP expression in GS4 cells; concentrations for the inhibitors are 100 units/ml IFN, 1 µM 2CMA and 2 µg/ml Cs A; both the mean Intensity of the GFP and the percentage of GFP-positive cells were effectively lowered by the inhibitors.
Figure 5:
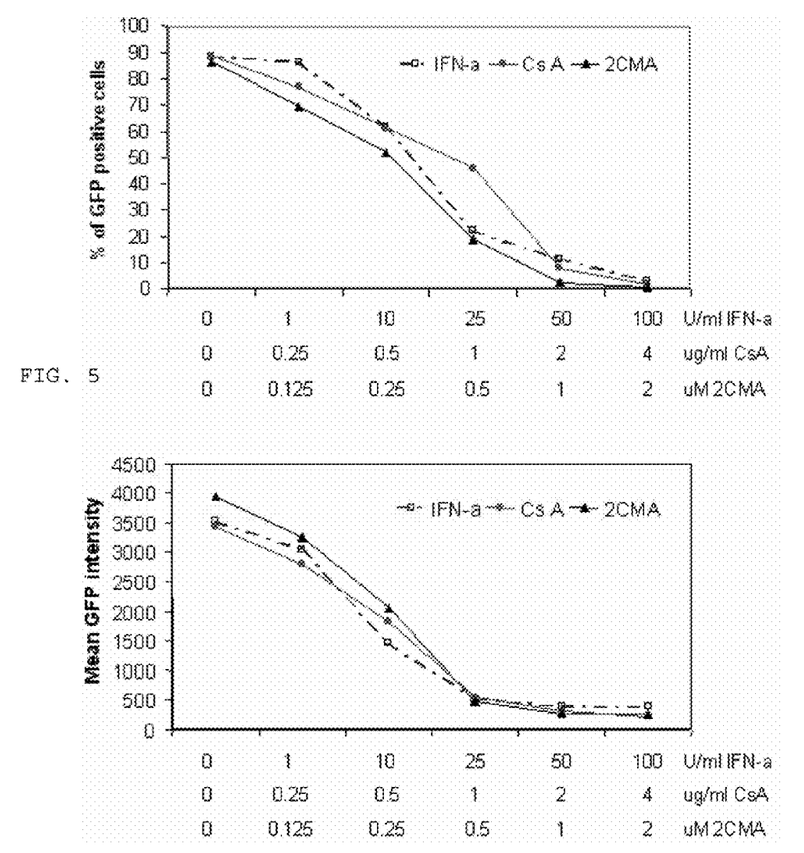
FIG. 5 illustrates dosage-dependent inhibition of NS5A-GFP expression by IFN, 2CMA and Cs A; the duration of treatment in D and E was 4 days.

The GFP signal of these cells was then analyzed by flow cytometry 4 days after treatment with increasing amounts of inhibitors, including Interferon-α (IFN-α), 2'-Cmethyl-adenosine (2CMA), and Cyclosporin A (Cs A). The inhibitors effectively reduced the percentage of GFP positive cells as well as the mean GFP intensity of the treated population (FIG. 4). Results for both parameters showed good dosage-dependent inhibition by the inhibitors (FIG. 5). The 1050 (0.25 μM for 2CMA, 0.5 μg/ml for CsA, and 10-25 units/ml for IFN-α) obtained with this assay closely resemble results from previous studies where HCV RNA level was measured (2, 6, 19, 26).

Figure 6:
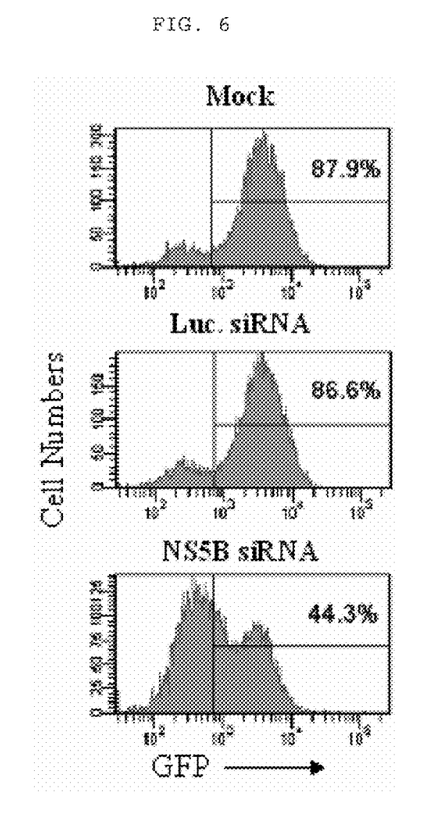
FIG. 6 depicts a small interfering RNA whose target is the genome of HCV inhibits NS5A-GFP expression of GS4 cells and provides FACS profiles of GS4 cells transduced with either a control (Luc. siRNA) or a siRNA whose target is the NS5B gene of the HCV 1 b; the cells were analyzed 4 days after transduction.
Figure 7:
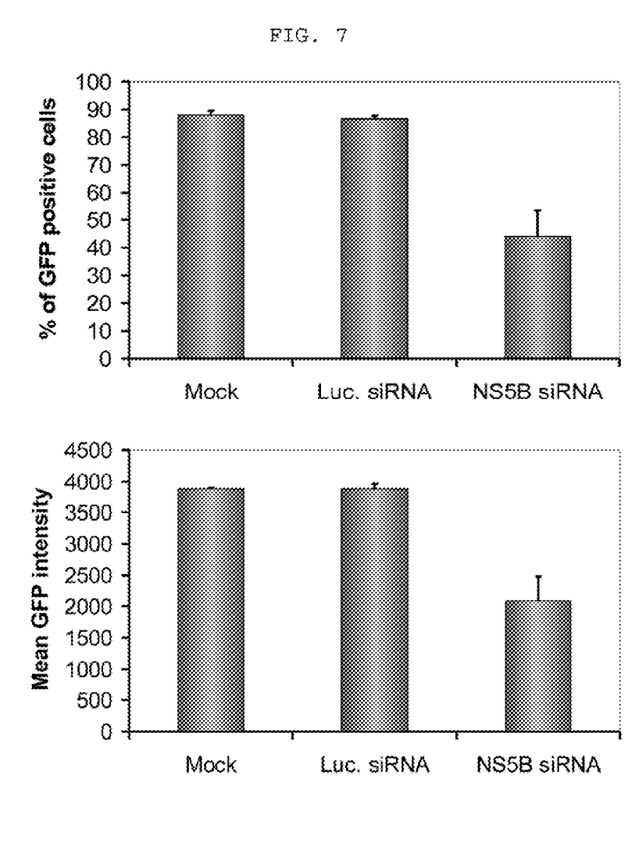
FIG. 7 is a quantitative representation of the siRNA-mediated inhibition with either the percentage of GFP-positive cells or mean GFP intensity as the measure.

We next determined whether a siRNA whose direct target is the HCV genome could suppress NS5A-GFP expression in GS4 cells by degrading viral RNA. We constructed lentiviral vectors that expressed the hairpin forms of siRNAs whose targets were either luciferase or the NS5B gene as previously described (25). The NS5B siRNA had been shown to inhibit RNA replication by targeting the HCV replicon RNA for degradation (27); the luciferase siRNA served as a negative control. When expressed in the GS4 cells, the NS5B siRNA, but not the luciferase siRNA, specifically inhibited NS5A-GFP expression (FIG. 6). We consistently observed 50-60% inhibition with the siRNA, corresponding to the transduction efficiency of the replicon cells with our lentiviral vectors (FIG. 7 and data not shown). Taken together, these results show that the GS4 cell line is a suitable indicator cell line for HCV replication and that the flow cytometry-based assay can be used to study replicon inhibition in vitro.

Figure 8:
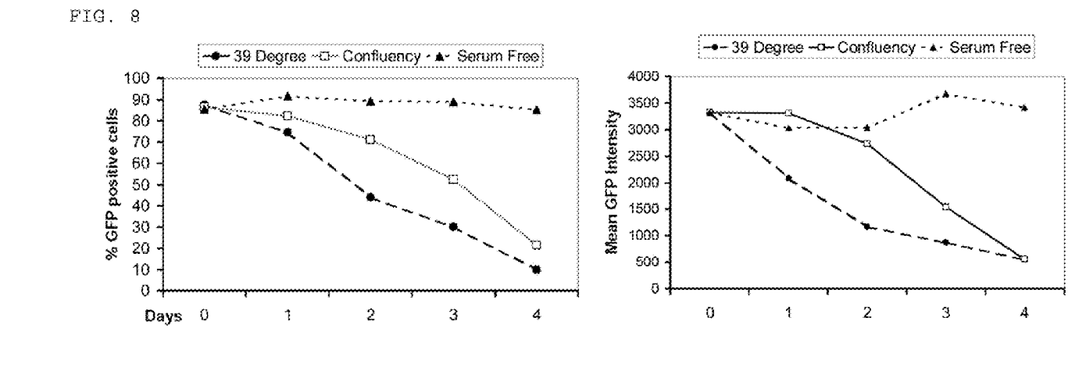
FIG. 8 shows cell confluency and serum starvation have drastically different effects on HCV replication, and a comparison of the effects on HCV expression by three nonchemical treatments: 39° C., confluency, and serum starvation; the cells were cultured under the indicated conditions for 4 days, and samples were taken each day for FACS analysis.
Figure 9:
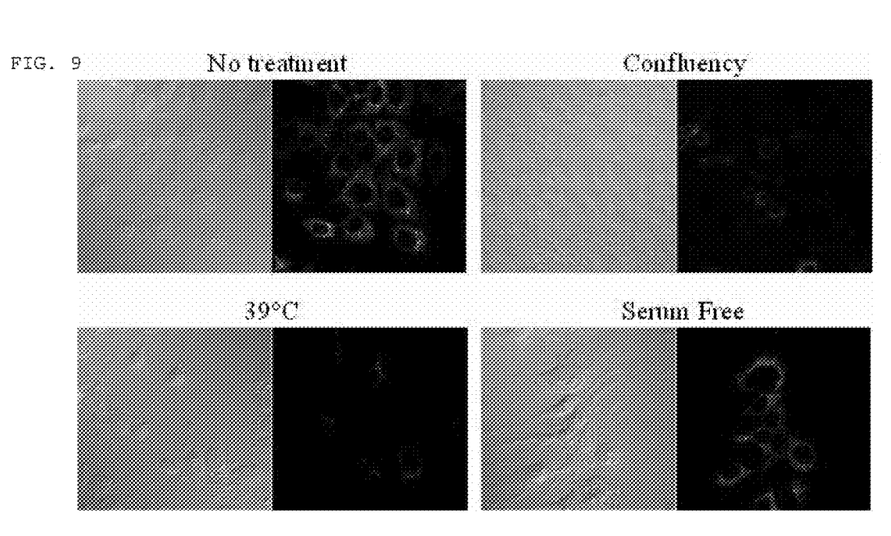
FIG. 9 depicts microscopic images (DIC and fluorescence) of the day 4 sample.
Figure 10:
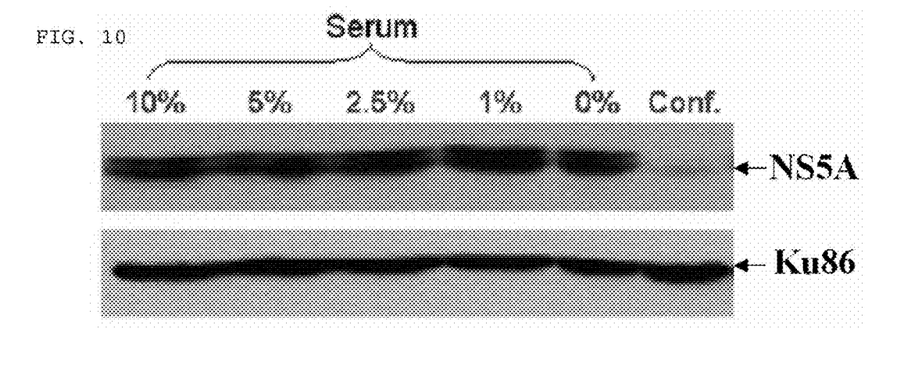
FIG. 10 shows that serum starvation failed to inhibit HCV expression in a replicon cell line without GFP; 1B replicon cells were cultured under the indicated conditions for 4 days and total proteins were extracted and then subjected to immunoblotting with an anti-NS5A antibody; after detection, the same membrane was stripped of the NS5A signal and probed again with an anti-Ku86 antibody as an internal control for protein loading.
Figure 11:
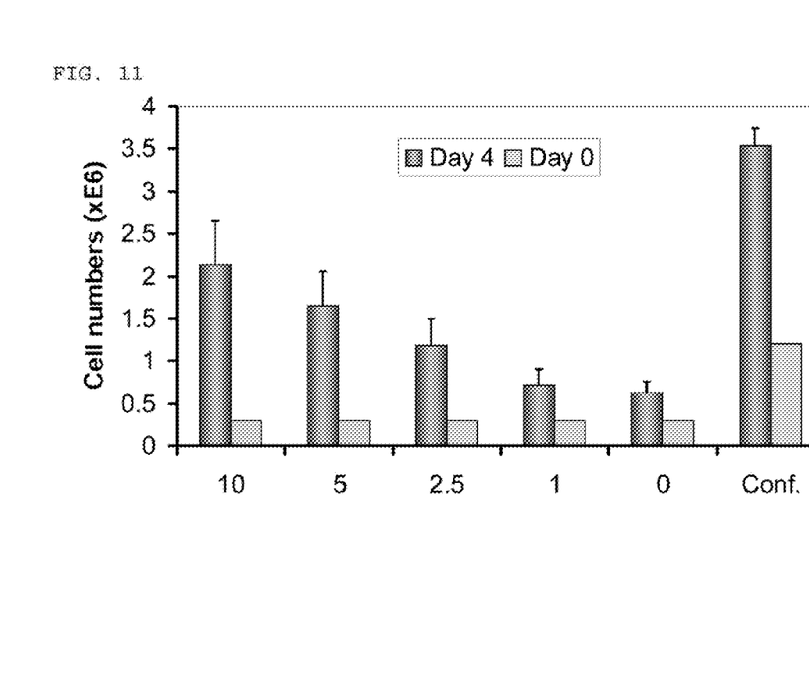
FIG. 11 illustrates serum starvation effectively arrested cell growth as expected; the cell numbers at the beginning (day 0) and the conclusion of the experiment (day 4) were quantified with a trypan blue exclusion assay.

Serum starvation does not inhibit HCV expression as cell confluency does. We applied this assay to test a number of non-drug-based treatments that had been reported to inhibit HCV replication in vitro. These included cell confluency, 39° C. incubation, and serum starvation. GS4 cells were treated for 4 days before FACS analysis. To our surprise, even though cell confluency and 39° C. treatment efficiently inhibited replicon as previously reported (7, 20, 22, 31), serum starvation had no effect even when cells were maintained in culture medium with 0% serum for 96 hours, after which the replicon cells started to die off (FIG. 8). Lack of inhibition of NS5A-GFP expression by serum starvation was also confirmed by fluorescence microscopy (FIG. 9). To rule out the possibility that the failure of serum starvation to suppress replicon expression is a result of our multiple rounds of cell sorting and specific to this GFP-containing replicon, we repeated the experiment using a different replicon cell line that does not contain GFP and had not been subjected to cell sorting. Cell line 1B is a replicon clone derived from a HCV-N based replicon (6, 9). We subjected these cells to serum starvation for 4 days and then detected NS5A expression using western blot. Decreasing amount of serum had no effect on the NS5A level, whereas confluency had a dramatic inhibitory effect (FIG. 10). On the other hand, serum starvation had a significant effect on cell growth (FIG. 11). Note that 1% or no serum had a greater effect on cell growth than did confluency yet had no effect on NS5A expression.

Figure 12:
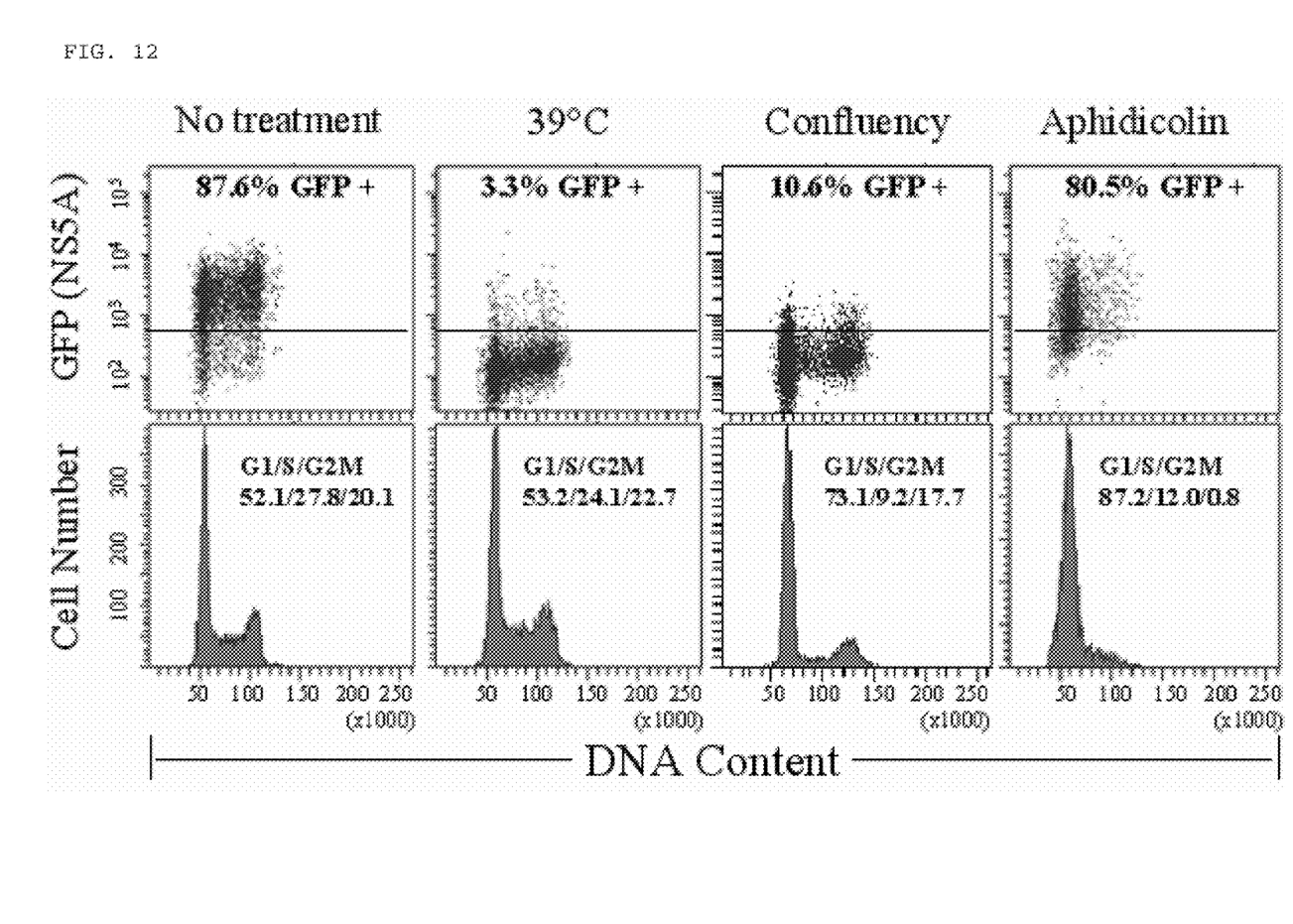
FIG. 12 shows the effect of aphidicolin on cell cycle and HCV expression; 1×106 GS4 cells were cultured under the indicated conditions for 4 days before being stained with propidium iodide for DNA analysis; the simultaneous cell-cycle and NS5A-GFP analysis was carried out on a FACS-Canto flow cytometer with the accompanying FACSDiva software (BD Biosciences); the concentrations of aphidicolin tested ranged from 5 to 20 µg/ml, and all failed to affect NS5A-GFP expression significantly; the result with 10 µg/ml aphidicolin is shown.

Cell cycle perturbation failed to suppress HCV replication and expression. Failure of growth arrest to inhibit replicon expression prompted us to examine the effect of cell-cycle perturbation on replicon expression. Propidium iodide (PI) staining of the cells permitted acquisition of dual fluorescence FACS profiles showing the cell-cycle distribution of GFP-positive and -negative cells. We found no correlation between positive GFP signal and any of the cell-cycle stages in the cycling cells (FIG. 12, no treatment). Incubation at 39° C. inhibited NS5A-GFP expression without any effect on cell-cycle profile. More importantly, although cell confluency inhibited HCV expression, aphidicolin failed to do so even though it effectively arrested cell cycle at the G1/S transition as expected (FIG. 12). Even though confluency also affected cell cycle to a certain degree, its effect on cell-cycle progress was far less dramatic than that of aphidicolin.

Figure 13:
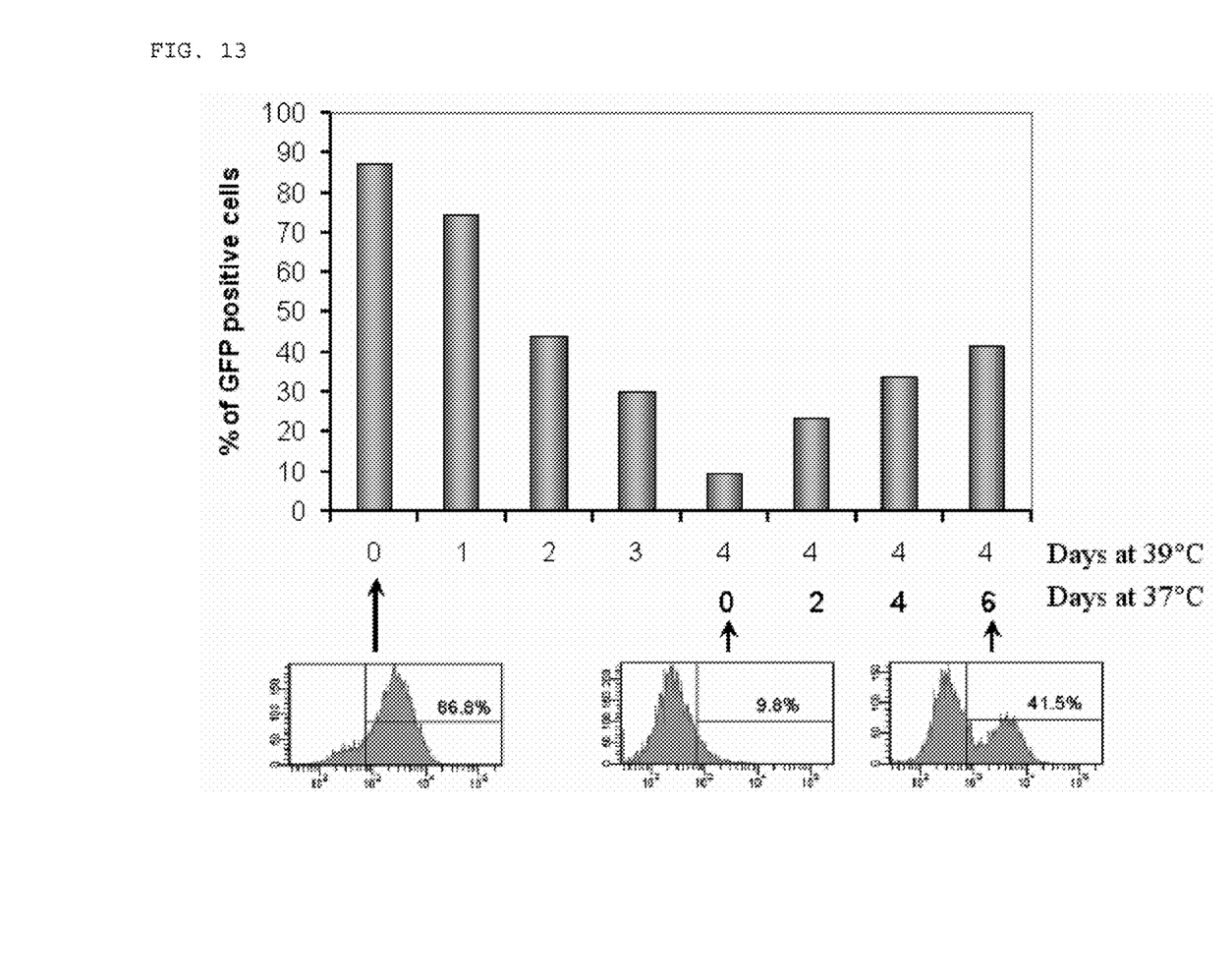
FIG. 13 shows that aphidicolin and serum starvation do not prevent resumption of HCV expression; inhibition of HCV replication by 39° C. treatment is reversible; the GS4 cells were cultured at 39° C. for 4 days then at 37° C. for another 6 days (cells were split when appropriate to prevent confluency); samples were taken for FACS every day during the 39° C. treatment period and every two days during the 37° C. recovery period.
Figure 14:
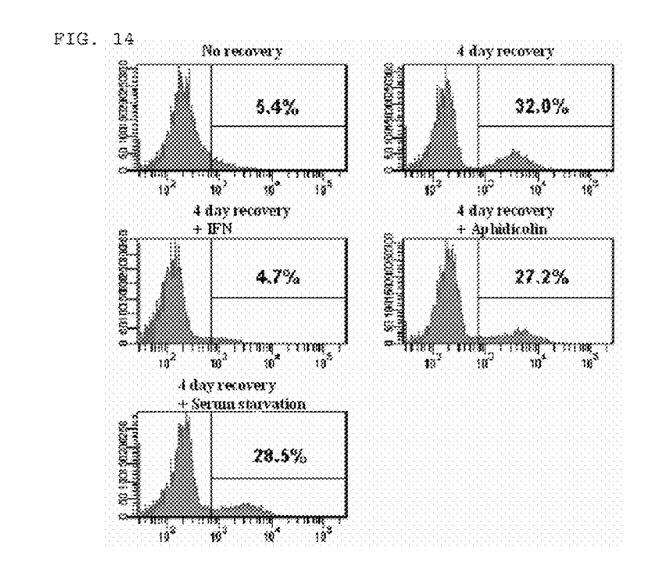
FIG. 14 indicates that neither aphidicolin nor serum starvation could prevent the recovery of HCV replication and expression; after 4 days in culture at 39° C., the GS4 cells were allowed to recover for 4 days at 37° C. in the presence of various inhibitors or in serum-free media; although 100 units/ml IFN-a efficiently blocked the resumption of HCV expression, 10 µg/ml aphidicolin and serum starvation failed to do so.
Figure 15:
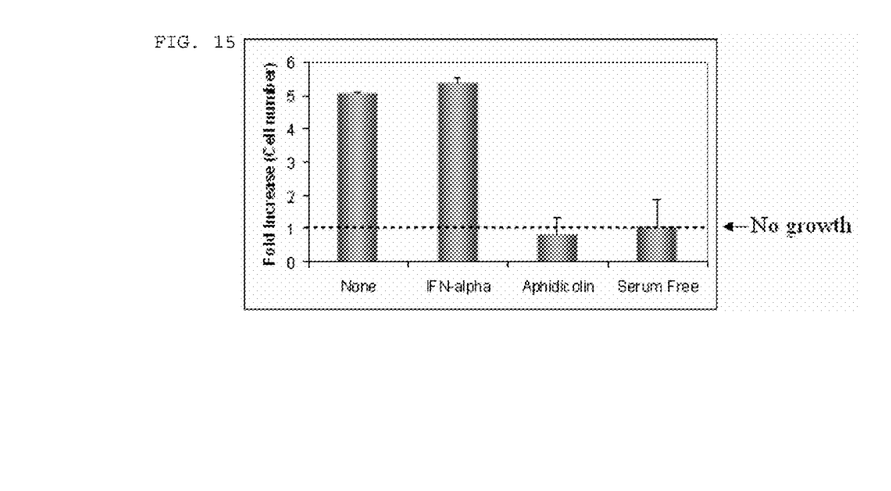
FIG. 15 shows that aphidicolin and serum starvation inhibited cell growth as expected; the same number of cells (2×105) were seeded for recovery for all samples; at the end of the experiment, the cell numbers in each sample were obtained with the trypan blue exclusion assay, and the fold of increase in cell numbers is shown.

To eliminate the possibility that these growth-arrest treatments somehow stabilize the GFP and maintain it throughout the treatment, we took advantage of our finding that 39° C. treatment results in reversible inhibition of HCV replication in our assay. We first eliminated the GFP signal from GS4 cells by incubating them at 39° C. for 4 days and then transferred the cells back to 37° C. so that HCV replication could recover. As shown in FIG. 13, over a recovery period of 6 days at 37° C., more than 40% of the cells regained the GFP signal, indicating HCV replication and viral protein expression had resumed. We tested aphidicolin and serum starvation using this assay along with IFN-α. Although IFN-a efficiently blocked the recovery of the NS5A-GFP expression in this assay, aphidicolin and serum starvation again did not prevent the resumption of HCV replication, which led to the recovery of NS5A-GFP expression (FIG. 14). Measurement of cell number in these samples during the course of the recovery indicated that aphidicolin and serum starvation effectively blocked cell growth as expected (FIG. 15). Taken together, these results show that neither serum starvation nor aphidicolin-induced cell-cycle arrest can produce the same inhibitory effect exerted by cell confluency.

Figure 16:
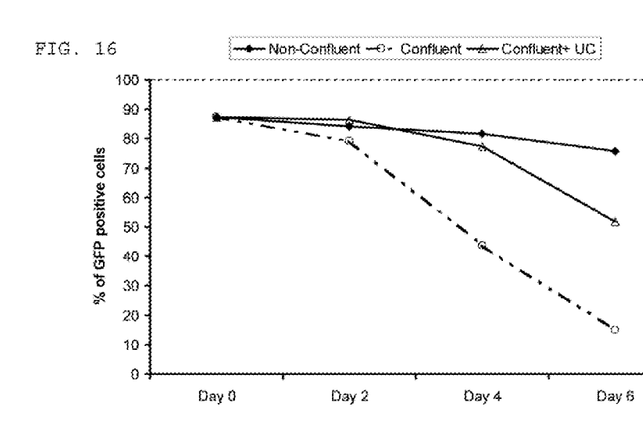
FIG. 16 illustrates that exogenous added nucleosides counteract the inhibitory effect of cell confluency; GS4 cells were cultured under either nonconfluent or confluent conditions for 6 days; one group of confluent cells was supplemented with uridine and cytidine (200 µM each) for the duration of the experiment; samples were taken for FACS analysis every two days.
Figure 17:
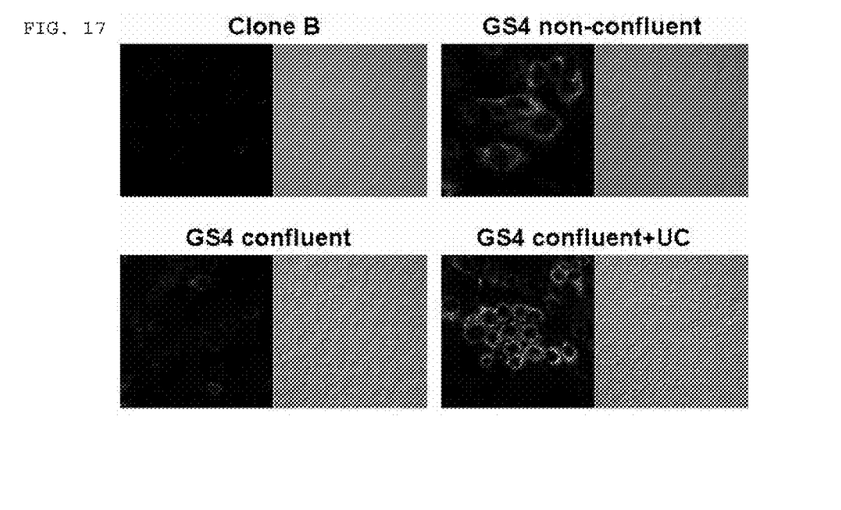
FIG. 17 depicts microscopic images (DIC and fluorescence) of the day 4 sample.

Reversal of confluency-mediated replicon inhibition by exogenous nucleosides. Inhibitors of de novo synthesis of nucleosides can suppress HCV replication (23), suggesting that lowered nucleoside level in confluent cells accounts for the reduction in viral RNA level. We tested this hypothesis by adding exogenous nucleosides to the culture media of confluent GS4 cells and then comparing the NS5AGFP expression with that of confluent cells without added nucleosides. Different nucleosides were tested, and the combination of uridine and cytidine (UC, 50-200 µM each) was found to rescue HCV expression to various degrees. A nearly complete reversal of the inhibitory effect was observed when the cells were kept in the confluency state for up to 4 days in the presence of 200 µM of UC, as demonstrated by both flow cytometry and fluorescence microscopy (FIGS. 16 and 17). The reversal is evident throughout the duration of the experiment (6 days after confluency) although longer incubation time in the confluent state caused the percentage of GFP-positive cells to decrease even in the cells to which UC had been added.

Figure 18:
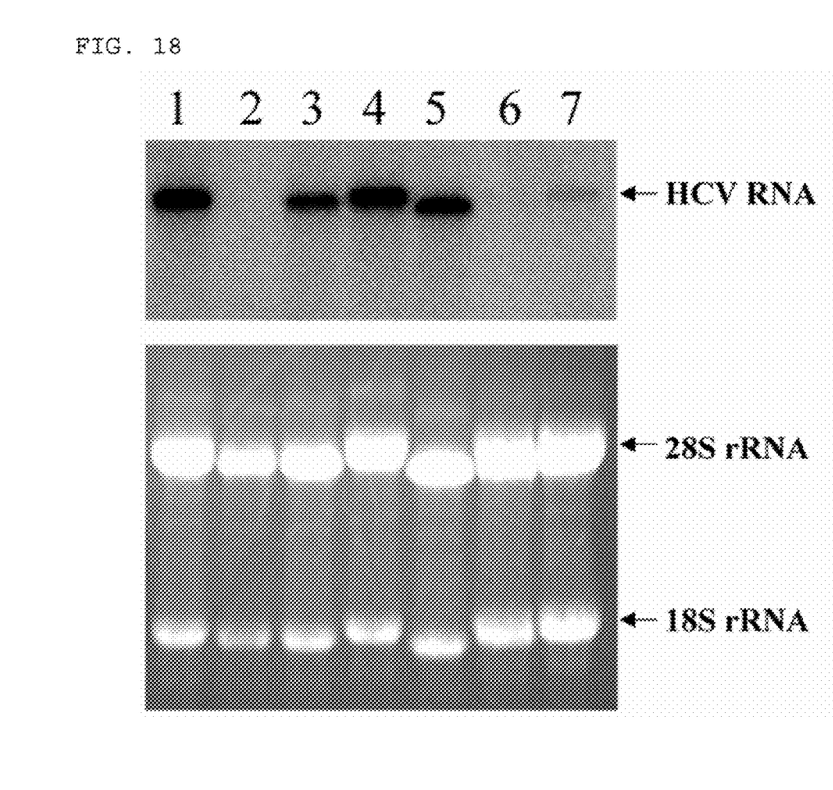

To validate our results at the viral RNA level, we repeated the inhibition and rescue experiments and directly examined HCV RNA by northern blotting. GS4 cells were treated with various inhibitors/agents for 3 days before the total RNAs were subjected to northern analysis for HCV RNA. 2CMA and cell confluency effectively eliminated HCV RNA signal (FIG. 18, top panel, lanes 2 and 6), whereas serum starvation had no effect (lane 4). Aphidicolin also only had a minimal effect, not enough to explain the confluency-based inhibition (lane 3). Importantly, exogenously added UC partially rescued RNA replication from confluency-based inhibition (compare lane 7 to lane 6). These results confirm that previous results obtained at the GFP expression level reflect HCV RNA replication.

Figure 19:
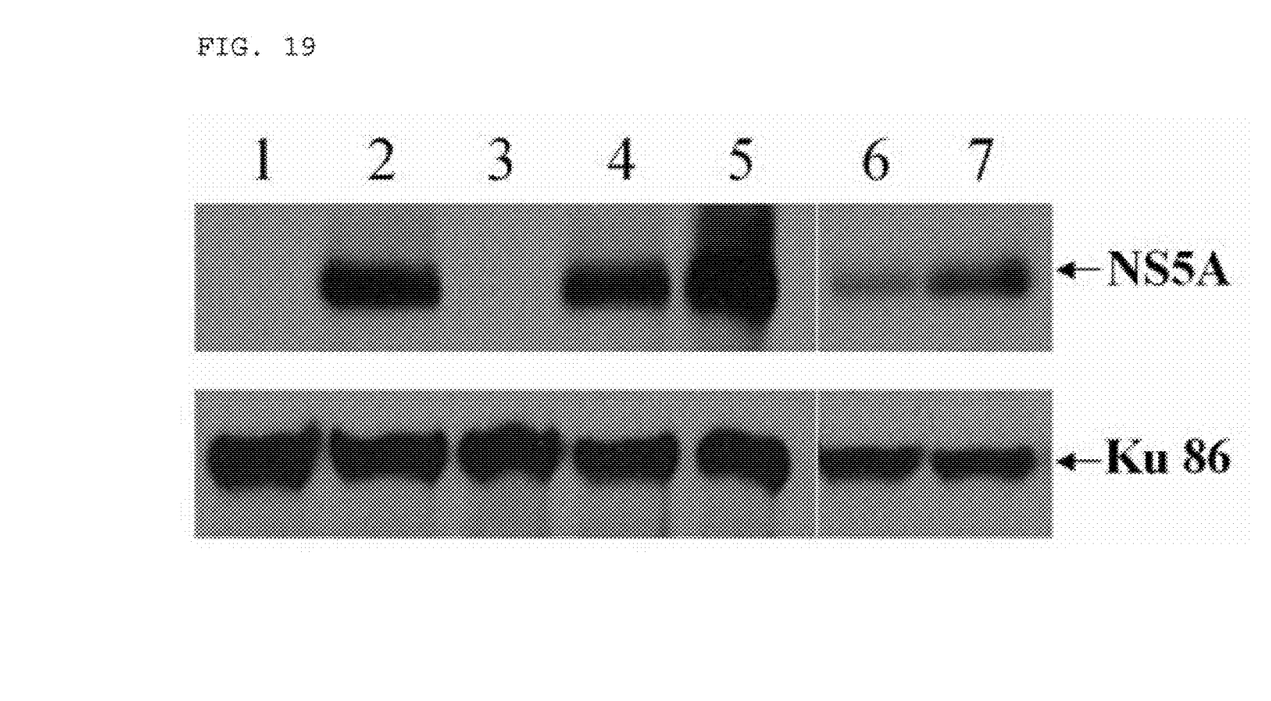
FIG. 19 shows that results obtained with a replicon containing wild-type HCV sequence are consistent with those of cell-culture-adapted replicons; Huh.8 cells were cultured under various conditions for 4 days before the total cell lysates were subjected to immunoblotting with anti-NS5A and anti-Ku86 antibodies; lane 1: Huh-7; lane 2: Huh.8 untreated, nonconfluent cells cultured in 10% serum; lane 3: 1 µM 2CMA; lane 4: 10 µg/ml aphidicolin; lane 5: 0% serum; lane 6: Huh.8 cells cultured under confluency; lane 7: Huh.8 cells cultured under confluency but with uridine and cytidine (200 µM each) added to the culture medium.

Additional experiments with a replicon cell line containing a wild type HCV sequence. We carried out additional experiments in a replicon cell line that does not contain the two modifications of GS4 cells: the S2204I mutation and the GFP insertion in NS5A. Huh.8 is replicon cell line that contains the wild-type sequence of NS5A (1). Huh.8 cells were cultured under various conditions for 4 days before being analyzed by western blot for NS5A expression. As a positive control, 1 µM of 2CMA effectively eliminated any NS5A expression; aphidicolin and serum starvation again did not inhibit HCV expression (FIG. 19). Serum starvation actually appeared to have increased NS5A expression, as it did with the GS4 cells (FIG. 8 and data not shown). In contrast, confluency inhibited NS5A expression, and more importantly, the exogenously added UC again counteracted this inhibition (FIG. 19, compare lanes 6 and 7). These data indicate that the lack of HCV inhibition by serum starvation and aphidicolin and the mechanism of confluency-based viral inhibition are not results of the modifications found in GS4 cells.

Discussion

We have previously used a GFP-based cell-sorting assay to identify cellular proteins involved in HIV replication (25) and wished to develop a similar assay for HCV replication in vitro. Taking advantage of a modified HCV replicon with the eGFP gene inserted into the coding region of NS5A (16), we obtained a derivative cell line that we named GS4 by live cell sorting and expansion. The GS4 cells we have developed have a much higher level of HCV expression than that of the original I/5A-GFP cells yet still respond very well to inhibitors. Even though the stronger GFP signal also makes it much easier to visualize the fluorescence under a microscope, the real strength of the assay based on the GS4 cells lies in its amenability to flow-cytometry analysis. The assay is simple and yet quantitative. No cell lysis or addition of exogenous substrates is needed. It is also rapid, and the results are visual. The speed of flow-cytometry analysis makes the test very fast, and many samples can be processed in parallel. It measures and displays results from individual cells, eliminating the need to normalize the results to cell numbers in different samples. This feature is especially important in situations where antiviral effects must be distinguished from those of cytostasis, for example in the case of cell confluency. Most importantly, the more favorable flowcytometry profile (minimized overlapping between the positive and the negative populations) makes it more suitable for screening projects using a reverse genetics approach, where distinct populations with desired fluorescence intensities can be recovered by cell sorting.

In the study reported here, we applied the assay to examine the effect of cell growth on HCV replication and the mechanism of cell confluency based inhibition of HCV RNA. The most straightforward mechanism for confluency-mediated inhibition is that exponential cell growth is required for efficient HCV replication. Indeed, other means of arresting cell growth have also been shown to inhibit HCV replication to various degrees (17, 22). In one study, serum starvation reduced the RNA abundance in a replicon cell harboring a selectable full-length HCV RNA based on the genotype 1b HCV-N, whereas aphidicolin treatment, which arrested the cell cycle as expected, had no effect on the abundance of HCV RNA or protein in these cells (22). In contrast, Murata et al. (17) observed an inhibitory effect by aphidicolin on HCV replicon in their report of TGF-β as an inhibitor of HCV replication in vitro. During the course of our study, we found that serum starvation or aphidicolin failed to inhibit HCV RNA replication or protein expression without killing the replicon cells, whereas cell confluency did so very effectively. TGF-β had only a marginal effect in our system (data not shown). The reason for the difference in the sensitivity of different replicons to these different treatments is not clear. Properties of specific replicons and sensitivities of different assays were some of the possibilities. We performed these experiments in three different replicon lines and used various assays including flow cytometry, fluorescence microscopy, western blotting, and northern blotting, and all gave similar results. In any event, because the replicon cells that we used here did respond as expected to cell confluency, we concluded that growth arrest was not the general mechanism of confluency-based viral inhibition. Note also that, because all these treatments significantly inhibit cell growth, the cell numbers at the time of the assay are dramatically lower in the treated group, making accurate normalization, for distinguishing antiviral from cytostatic effects, difficult. Because our flow cytometry-based assay looks at the HCV protein expression in individual cells, it does not need the normalization.

A second hypothesis, not mutually exclusive with that of growth arrest, is that the reduced intracellular pools of nucleosides account for the decrease of HCV RNA in confluent cells because these cells depend on salvage nucleoside biosynthesis pathways and thus have a lower level of intracellular NTPs. We reasoned that, if this were the case, adding back exogenous nucleoside should alleviate the block on HCV replication and rescue viral expression. Our results indicate that this was indeed at least partly the case, as exogenously added uridine and cytidine rescued HCV RNA replication and protein expression in confluent cells of several different replicon lines. These exogenous nucleosides probably rescue HCV replication by increasing the level of building blocks for the synthesis of viral genome RNA. The failure of the nucleosides to reverse completely the inhibitory effect posed by confluency beyond four days suggests that additional mechanisms exist for confluency-based HCV inhibition.

The finding that serum starvation and cell confluency have drastically different effects on steady-state HCV replicon RNA level is somewhat surprising, as they both induce a cytostatic state of the cells that is believed to be detrimental to HCV replication. Our results nevertheless suggest that serum starvation and confluency cause distinct changes in the physiological state of the cells that is relevant for HCV replication. The results with exogenously added nucleosides imply that serum starvation does not result in the reduction of intracellular NTP pools as confluency does, at least not to the extent that it limits HCV replication.

Cell growth/cycle arrest induced by serum starvation or aphidicolin has been reported to increase replication/infection of other viruses (5, 15). The transcription of the Borna disease virus (BDV), a negative-stranded RNA virus, was enhanced by serum starvation. Interestingly, the RNA species that was up-regulated the most was the 1.9-Kb RNA without the 5' cap and 3' poly (A) tail, similar to the HCV genomic RNA (15). The finding that serum starvation can increase HCV expression under certain culture conditions is intriguing.

The dynamics of HCV replication in response to cellular environment may be relevant in vivo, as detection of HCV in pathologic samples has been variable, possibly because replication levels fluctuate. The exquisite sensitivity of HCV replication to intracellular nucleoside level may provide an explanation for the difficulty of detecting and recovering large quantities of viruses in vivo.

Hence, the present invention includes a method of maintaining hepatitis C virus (HCV) replicating indefinitely in cell culture, the method comprising providing a culture of cells susceptible to infection by HCV, introducing to the cell culture an inoculum containing an infective dose of HCV, contacting the inoculated cell culture with a growth medium containing uridine and cytidine, and adding exogenous uridine and cytidine to avoid lowered levels of nucleosides in the cell culture.

Accordingly, in the drawings and specification there have been disclosed typical preferred embodiments of the invention and although specific terms may have been employed, the terms are used in a descriptive sense only and not for purposes of limitation. The invention has been described in considerable detail with specific reference to these illustrated embodiments. It will be apparent, however, that various modifications and changes can be made within the spirit and scope of the invention as described in the foregoing specification and as defined in the appended claims.

REFERENCES

1. Blight, K. J., A. A. Kolykhalov., and C. M. Rice. 2000. Efficient initiation of HCV RNA replication in cell culture. Science 290:1972-1974.
2. Carroll, S. S., J. E. Tomassini, M. Bosserman, K. Getty, M. W. Stahlhut, A. B, Eldrup, B. Bhat, D. Hall, A. L. Simcoe, R. LaFemina, C. A. Rutkowski, B. Wolanski, Z. Yang, G. Migliaccio, R. De Francesco, L. C. Kuo, M. MacCoss, and D. B. Olsen. 2003. Inhibition of hepatitis C virus RNA replication by 2'-modified nucleoside analogs. J. Biol. Chem. 278:11979-11984.
3. Foy, E., K. Li, C. Wang, R. Sumpter Jr., M. Ikeda, S. M. Lemon, and M. Gale Jr. 2003. Regulation of interferon regulatory factor-3 by the hepatitis C virus serine protease. Science 300:1145-1148.
4. Friebe, P. and R. Bartenschlager. 2002. Genetic analysis of sequences in the 3' nontranslated region of hepatitis C virus that are important for RNA replication. J. Virol. 76: 5326-5338.
5. Groschel, B. and F. Bushman. 2005. Cell cycle arrest in G2/M promotes early steps of infection by human immunodeficiency virus. J. Virol. 79:5695-5704.
6. Guo, J. T., V. V. Bichko, and C. Seeger. 2001. Effect of alpha interferon on the hepatitis C virus replicon. J. Virol. 75:8516-8523.
7. Guo, J. T., J. A. Sohn, Q. Zhu, and C. Seeger. 2004. Mechanism of the interferon alpha response against hepatitis C virus replicons. Virology 325:71-81.
8. Horscroft, N., V. C. Lai, W. Cheney, N. Yao, J. Z. Wu, Z. Hong, and W. Zhong. 2005. Replicon cell culture system as a valuable tool in antiviral drug discovery against hepatitis C virus. Antivir Chem Chemother. 16:1-12.
9. Ikeda, M., M. Yi, K. Li, and S. M. Lemon. 2002. Selectable subgenomic and genome-length dicistronic RNAs derived from an infectious molecular clone of the HCV-N strain of hepatitis C virus replicate efficiently in cultured Huh7 cells. J. Virol. 76:2997-3006.
10. Kolykhalov, A. A., K. Mihalik, S. M. Feinstone, and C. M. Rice. 2000. Hepatitis C virus-encoded enzymatic activities and conserved RNA elements in the 3' nontranslated region are essential for virus replication in vivo. J. Virol. 74:2046-2051.
11. Krieger, N., V. Lohmann, and R. Bartenschlager. 2001. Enhancement of hepatitis C virus RNA replication by cell culture-adaptive mutations. J. Virol. 75:4614-4624.
12. Lamarre, D., P. C. Anderson, M. Bailey, P. Beaulieu, G. Bolger, P. Bonneau, M. Bos, D. R. Cameron, M. Cartier, M. G. Cordingley, A. M. Faucher, N. Goudreau, S. H. Kawai, G. Kukolj, L. Lagace, S. R. LaPlante, H. Narjes, M. A. Poupart, J. Rancourt, R. E. Sentjens, R. St George, B.

Simoneau, G. Steinmann, D. Thibeault, Y. S. Tsantrizos, S. M. Weldon, C. L. Yong, and M. Llinas-Brunet. 2003. An NS3 protease inhibitor with antiviral effects in humans infected with hepatitis C virus. Nature. 426:186-189.
13. Lindenbach, B. D., M. J. Evans, A. J. Syder, B. Wolk, T. L. Tellinghuisen, C. C. Liu, T. Maruyama, R. O. Hynes, D. R. Burton, J. A. McKeating, and C. M. Rice. 2005. Complete replication of hepatitis C virus in cell culture. Science. June 9; [Epub ahead of print]
14. Lohmann, V., F. Korner, J, Koch, U. Herian, L. Theilmann, and R. Bartenschlager. 1999. Replication of subgenomic hepatitis C virus RNAs in a hepatoma cell line. Science 285:110-113.
15. Mizutani, T., H. Inagaki, D. Hayasaka, H. Kariwa, and I. Takashima. 1999. Enhancement of Borna disease virus transcription in persistently infected cells by serum starvation. J. Vet. Med. Sci. 61:831-834.
16. Moradpour, D., M. J. Evans, R. Gosert, Z. Yuan, H. E. Blum, S. P. Goff, B. D. Lindenbach, and C. M. Rice. 2004. Insertion of green fluorescent protein into nonstructural protein 5A allows direct visualization of functional hepatitis C virus replication complexes. J. Virol. 78:7400-7409.
17. Murata, T., T. Ohshima, M. Yamaji, M. Hosaka, Y. Miyanari, M. Hijikata, and K. Shimotohno. 2005. Suppression of hepatitis C virus replicon by TGF-beta. Virology 331: 407-417.
18. Murray, E. M., J. A. Grobler, E. J. Markel, M. F. Pagnoni, G. Paonessa, A. J. Simon, and O. A. Flores. 2003. Persistent replication of hepatitis C virus replicons expressing the beta-lactamase reporter in subpopulations of highly permissive Huh7 cells. J. Virol. 77:2928-2935.
19. Nakagawa, M., N. Sakamoto, N. Enomoto, Y. Tanabe, N. Kanazawa, T. Koyama, M. Kurosaki, S. Maekawa, T. Yamashiro, C. H. Chen, Y. Itsui, S. Kakinuma, and M. Watanabe. 2004. Specific inhibition of hepatitis C virus replication by cyclosporin A. Biochem. Biophys. Res. Commun. 313:42-47.
20. Pietschmann, T., V. Lohmann, G. Rutter, K. Kurpanek, and R. Bartenschlager. 2001. Characterization of cell lines carrying self-replicating hepatitis C virus RNAs. J. Virol. 75:1252-1264.
21. Randall, G., and C. M. Rice. 2004. Interfering with hepatitis C virus RNA replication. Virus. Res. 102:19-25.
22. Scholle, F., K. Li, F. Bodola, M. Ikeda, B. A. Luxon, and S. M. Lemon. 2004. Virus-host cell interactions during hepatitis C virus RNA replication: impact of polyprotein expression on the cellular transcriptome and cell cycle association with viral RNA synthesis. J. Virol. 78:1513-1524.
23. Stuyver, L. J., T. R. McBrayer, P. M. Tharnish, A. E. Hassan, C. K. Chu, K. W. Pankiewicz, K. A. Watanabe, R. F. Schinazi, and M. J. Otto. 2003. Dynamics of subgenomic hepatitis C virus replicon RNA levels in Huh-7 cells after exposure to nucleoside antimetabolites. J. Virol. 77:10689-10694.
24. Wakita, T., T. Pietschmann, T. Kato, T. Date, M. Miyamoto, Z. Zhao, K. Murthy, A. Habermann, H. G. Krausslich, M. Mizokami, R. Bartenschlager, and T. J. Liang. 2005. Production of infectious hepatitis C virus in tissue culture from a cloned viral genome. Nat Med. June 12; [Epub ahead of print]
25. Waninger, S., K. Kuhen, X. Hu, J. E. Chatterton, F. Wong-Staal, and H. Tang. 2004. Identification of cellular cofactors for human immunodeficiency virus replication via a ribozyme-based genomics approach. J. Virol. 78:12829-12837.
26. Watashi, K., M. Hijikata, M. Hosaka, M. Yamaji, and K. Shimotohno. 2003. Cyclosporin A suppresses replication of hepatitis C virus genome in cultured hepatocytes. Hepatology. 38:1282-1288.
27. Wilson, J. A., S. Jayasena, A. Khvorova, S. Sabatinos, I. G. Rodrigue-Gervais, S. Arya, F. Sarangi, M. Harris-Brandts, S. Beaulieu and C. D. Richardson. 2003. RNA interference blocks gene expression and RNA synthesis from hepatitis C replicons propagated in human liver cells. Proc. Natl. Acad. Sci. U.S.A. 100:2783-2788.
28. Yi, M., F. Bodola, and S. M. Lemon. 2002. Subgenomic hepatitis C virus replicons inducing expression of a secreted enzymatic reporter protein. Virology. 304:197-210.
29. Yi, M., and S. M. Lemon. 2003. Structure-function analysis of the 3' stem-loop of hepatitis C virus genomic RNA and its role in viral RNA replication. RNA. 9:331-345.
30. Zhong, J., P. Gastaminza, G. Cheng, S. Kapadia, T. Kato, D. R. Burton, S. F. Wieland, S. L. Uprichard, T. Wakita, and F. V. Chisari. 2005. Robust hepatitis C virus infection in vitro. Proc. Natl. Acad. Sci. USA. 102:9294-9299. Epub 2005 Jun. 6.
31. Zhu, Q., J. T. Guo, and C. Seeger. 2003. Replication of hepatitis C virus subgenomes in nonhepatic epithelial and mouse hepatoma cells. J. Virol. 77:9204-9210.

That which is claimed:

1. A method of maintaining hepatitis C virus (HCV) replicating in a cell culture under confluence contact inhibition, the method comprising:
   incubating a cell culture infected with HCV until the cells reach confluence; and
   adding exogenous uridine and cytidine to avoid lowered levels of nucleosides in the cell culture.

2. A method of at least partially rescuing hepatitis C virus (HCV) replication in a cell culture wherein said replication is under confluence contact inhibition, the method comprising adding exogenous uridine and cytidine to the cell culture.

3. The method of claim 1 or claim 2 wherein the exogenous uridine and cytidine are added in effective amounts of at least 50 µM each.

4. A method of maintaining hepatitis C virus (HCV) replication in a cell culture under confluence contact inhibition, the method comprising providing the cell culture infected with HCV a growth medium containing free nucleoside uridine and cytidine in effective amounts, wherein the effective amounts of uridine and cytidine are from approximately 50 to at least approximately 200 µM of each.

* * * * *